United States Patent [19]

Mortazavi

[11] Patent Number: 5,040,538
[45] Date of Patent: Aug. 20, 1991

[54] PULSED LIGHT BLOOD OXYGEN CONTENT SENSOR SYSTEM AND METHOD OF USING SAME

[75] Inventor: Said Mortazavi, Granada Hills, Calif.

[73] Assignee: Siemens-Pacesetter, Inc., Sylmar, Calif.

[21] Appl. No.: 403,208

[22] Filed: Sep. 5, 1989

[51] Int. Cl.⁵ ............................................. A61B 5/00
[52] U.S. Cl. ................................................ 128/633
[58] Field of Search ............... 128/633, 634, 664, 665, 128/666

[56] References Cited

U.S. PATENT DOCUMENTS

| | | | |
|---|---|---|---|
| 3,871,362 | 3/1975 | Dunegan | 128/666 |
| 4,202,339 | 5/1980 | Wirtzfeld et al. | 128/419 |
| 4,267,844 | 5/1981 | Yamanishi | 128/633 |
| 4,399,820 | 8/1983 | Wirtzfeld et al. | 128/419 |
| 4,727,879 | 3/1988 | Liess | 128/633 |
| 4,750,495 | 6/1988 | Moore et al. | 128/419 |
| 4,791,935 | 12/1988 | Baudino et al. | 128/637 |
| 4,807,629 | 2/1989 | Baudino et al. | 128/419 |
| 4,813,421 | 3/1989 | Baudino et al. | 128/633 |
| 4,815,469 | 3/1989 | Cohen et al. | 128/634 |

Primary Examiner—William E. Kamm
Attorney, Agent, or Firm—Leslie S. Miller

[57] ABSTRACT

A sensor for use with a rate-responsive pacemaker is disclosed which is responsive to blood oxygen content, thereby allowing the cardiac rate of the pacemaker to closely mimic the natural response pattern of the heart to changing physiological need. The sensor integrates the output from a photosensor driven by blood-reflected light from an LED, and when the integrated output reached a predetermined threshold latches the circuit, enabling the use of time to indicate the level of blood oxygen content. The sensor thus advantageously requires neither a voltage doubler in the driving circuitry, or an analog-to-digital converter in the output circuitry, reducing both complexity and power consumption of the blood oxygen sensor.

25 Claims, 3 Drawing Sheets

PULSED LIGHT BLOOD OXYGEN CONTENT SENSOR SYSTEM AND METHOD OF USING SAME

BACKGROUND OF THE INVENTION

FIELD OF THE INVENTION

The present invention relates generally to a rate-responsive cardiac pacemaker, and more particularly to a sensor for a rate-responsive pacemaker which is responsive to blood oxygen content, thereby allowing the cardiac rate to closely mimic the natural response pattern of the heart to changing physiological need.

The cardiac pacemaker is perhaps one of the best known electronic marvels of modern medicine, and the implantation of a pacemaker in a patient has become almost a routine operation. The small, electronic device pulses the heart of the patient continuously over an extended period of time, or, in the case of demand pacemakers, monitors the heart's natural operation and provides stimulating pulses only when the heart skips a beat. Pacemakers allow patients with heart problems which would have been either fatal or incapacitating without a pacemaker to resume relatively normal lives.

It will be realized by those skilled int he art that the modern pacemaker is a highly complex device, capable of event sensing, two-way telemetry, and sensing and packing in either ore both of the atrium and the ventricle of the heart. Such pacemakers may be finely tuned by the physician subsequent to implant, and the parameters tweaked to result in optimum pacing performance.

Despite the impressive sophistication of such pacemakers, they represent a compromise due to a single major difference between the healthy heart and a paced heart--namely, the response to activity, exercise, or stress. A healthy heart is create responsive to a number of factors including physical activity or exercise. Variations in the cardiac stroke volume and systemic vascular resistance occur in the cardiovascular system due to physiological stresses such as exercise, temperature changes, postural changes, emotion, hypoglycemia, Valsalva maneuvers, etc.

To maintain adequate perfusion pressure and cardiac output under these stresses, it is necessary to adjust hearth rate. The healthy heart may beat at 60 or fewer beats per minute during response or sleep, and at 120 or more beats per minute during strenuous exercise, for example. The heart paced by a pacemaker which is non-rate responsive will typically beat at a constant rate of approximately 70 beats per minute.

It will be appreciated that the paced heart will supply more blood than is needed during sleep, and may even prevent the patient from sleeping restfully. Even more seriously, patients paced at 70 beats per minute experience substantial difficulty in engaging in strenuous activity. A moderate level of activity such as walking will cause difficulty in some patients. It is apparent that a pacemaker which varies in response to physiological need represents a highly desirable device which will enable a normal active life for patients requiring a pacemaker.

Physiological responsive cardiac pacing must optimize cardiac rate to the level of metabolic need in the absence of normal variable cardiac rate. The simplest answer to this problem is atrial tracking pacing, where the patient has a full or partial AV block and a dual chamber pacemaker pulses the ventricle in response to normal cardiac activity sensed in the atrium. However, this technique is not possible in many patients with sinus bradycardia or atrial fibrillation, and so rate-responsive pacing is necessary to mimic the normal variable cardiac rate.

A variety of physiological responsive pacing systems have been proposed, with the systems using a variety of physiological parameters as the basis for varying cardiac rate. These parameters include blood temperature, various sensed timing signals from the heart, pressure measured within the heart, respiratory rate, nervous system activity, physical activity, and blood chemistry. These systems will be discussed briefly below, and the problems inherent in each of the systems will become evident.

Venous blood temperature is measured in the right ventricle by Cook et al. in U.S. Pat. No. 4,436,092. Since blood temperature has been found to rise during exercise and the corresponding body core temperature increase, blood temperature indicates greater physiological need for blood supply. However, the response of such a system in quite slow. In addition, the system is inexact due to the coarseness at which measurements may be taken, the ingestion of cold liquids, and the effect caused by presence of a fever.

Both the QT interval and the P wave have been used to vary heart rate. The use of the QT interval is discussed in U.S. Pat. No. 4,228,803, to Rickards, and involves detection of the repolarization T wave subsequent to pacemaker stimulation (indicating the Q wave). A shorter QT interval is used to produce a higher paced cardiac rate. This system is slow in response, and not highly specific due to variations caused both by drugs ingested and by the used of pacemaker stimulation rather than using sensed contractions.

The use of the P wave is taught in U.S. Pat. No. 4,313,442, to Knudson et al. By responding to average atrial rate through detection of the P wave, the system varies cardiac rate. This is little more than a dual chamber system, and, as mentioned above, this technique is not possible in many patients with sinus bradycardia or atrial fibrillation. It is also slow due to time averaging, and possibly subject to errors due to faulty signal detection which could drive the heart at a greater that desired rate.

The pressure of blood may be used to determine an appropriate heart rate. Using blood pressure within the heart to regulate heart rate has been the basis for several proposed systems, beginning with the system shown in U.S. Pat. No. 3,358,690, to Cohen. Cohen uses a pressure sensor in the atrium to detect a high pressure condition, and, after a short delay, provides a pacing pulse to the ventricle. This system also assumes that the atrium is operating completely normally, and thus it is not possible to use this system in many patients with sinus bradycardia or atrial fibrillation.

U.S. Pat. No. 3,857,399, to Zacouto, teaches a system that measures either left ventricle pressure or intramyocardial pressure using a sensor located in the left ventricle. This is absolutely unacceptable, since to introduce a sensor through the interventricular septum would be dangerous to say the least. Likewise, a cutdown or percutaneous introduction of such a sensor into the heart through an artery would result in necrosis of the artery.

U.S. Pat. No. 4,566,456, to Koning et al., uses a pressure sensor in the right ventricle, and, in response to either the pressure sensed or the time derivative of pressure sensed, provides a pacing pulse to the right ventricle. This system also assumes that the atrium is operating completely normally, and so it is not possible to use this system in many patients with sinus bradycardia or atrial fibrillation.

Finally, U.S. Pat. No. 4,600,017, to Schroeppel, teaches the use of a pressure sensor in the right ventricle to sense the closing of the tricuspid valve, and provides a pacing pulse thereafter. Once again, if the atrium is not operating completely normally it is not possible to use this system.

A respiratory rate sensor is shown in U.S. Pat. No. 3,593,718, to Krasner. An increase in respiratory rate causes a the system to produce a higher paced cardiac rate. Cardiac rate does not exactly track respiratory rate in the normal heart, and the problem with the Krasner device is that it is either too slow if respiratory rate is time-averaged, or it may be too fast if instantaneous respiratory rate is used. In addition, the system uses variations in chest impedance to produce a signal, making it both subject to false signals due to a variety of causes including loose sensors, and highly subject to damage from defibrillation.

Activities of the central nervous system are highly relevant to modification of cardiac rate. One use of nerve impulses is detailed in U.S. Pat. No. 4,201,219, to Bozal Gonzales, in which a neurodetector device is used to generate electrical signals indicative of nerve impulses. The frequency of the impulses is utilized to modify the paced cardiac rate. The implementation of this is considerably difficult, in that a stable, predictable coupling to the Hering nerve is required. In addition, it is difficult to discriminate between the signals detected to obtain the single signal desired, in that the technology involved is still in its infancy. This approach, while probably having a fast response, thus has neither the sensor reliability nor the system specificity necessary for a reliable product.

The approach which has found its way into the first generation of commercially available pacemakers is the activity sensing variable rate device, which varies rate in response to body movement. As body movement increases, so does the output from the sensor, typically a piezoelectric device producing an electrical output in response to vibratory movement induced by body movement. Increasing output from the sensor causes the system to produce a higher paced cardiac rate. Examples of such devices are illustrated in U.S. Pat. No. 4,140,132, to Dahl, and in U.S. Pat. No. 4,428,378, to Anderson et al.

Activity sensing variable rate pacemakers have a fast response and good sensor reliability. However, they are less than ideal in system specificity. For example, if a person with such a pacemaker was restfully riding in a car on a very bumpy road, his heart rate would increase dramatically at a time when such an increase was not warranted, and, indeed, would not be initiated by the normal healthy heart. Similarly, if the person was pedaling at a furious rate on an exercise bicycle while his upper body were relatively motionless, he would likely run out of oxygen and pass out. Despite the commercial implementation of such devices, it will therefore be appreciated that they are far from perfect.

The last approach which has been taken is to use blood chemistry sensors to detect blood pH or oxygen saturation. The use of pH sensing is taught in U.S. Pat. No. 4,009,721, to Alcidi, and in U.S. Pat. No. 4,252,124, to Mauer et al. A membrane pH sensor electrode is typically placed in the right ventricle, and senses pH, which is proportional to the blood concentration of carbon dioxide, which is generated in increasing amounts by exercise. A diminution in the pH level is used to produce a higher paced cardiac rate. The speed of this system is slow, and sensor reliability over an extended lifetime is not yet great enough to produce a reliable product.

The use of oxygen saturation is shown in U.S. Pat. No. 4, 202,339, to Wirtzfeld et al, in U.S. Pat. No. 4,399,820, to Wirtzfeld et al., in U.S. Pat. No. 4,467,807, to Bornzin, and in U.S. Pat. No. 4,815,469, to Cohen et al. An optical detector is used to measure the mixed venous oxygen saturation, typically in the right ventricle. A diminution in the mixed venous oxygen saturation is used to produce a higher paced cardiac rate. The speed of this system is comparable to the time constant of the body, and sensor reliability and life has been greatly improved to the point where oxygen saturation sensors are fairly reliable devices.

Oxygen saturation systems typically operate using a current source to drive a circuit including the parallel combination of a phototransistor and a resistor in parallel, which combination is connected in series with an LED. The voltage across the circuit is monitored, with the relatively small variation in voltage being indicative of the full scale of oxygen saturation. The voltage across the LED will remain relatively constant, with the amount of current flowing through the resistor determining the voltage across the parallel combination of the phototransistor and the resistor. Despite the resulting variation in voltage across the circuit being small, typically less than 100 mV full scale, it is capable of providing an accurate indication of oxygen saturation.

One of the problems in such circuits is that they are inordinately sensitive to variations in the current source. Typically, a change in the output current from the current source by a given percentage will result in a percentage variation in the voltage range by an order of magnitude. Thus, a one percent change in output current from the current source will result in a variation of at least ten percent of the full scale of voltage variation. The implication of this fact is that the construction of the current source must be highly accurate to maintain even modest accuracy in the measurement of voltage to determine oxygen saturation.

An example of this high degree of sensitivity to a small variation in output current from the current source is helpful in understanding the problem. Assume that the output current from the current source is 1 mA, that the resistor is K$\Omega$, and the full scale variation in voltage across the circuit is 100 mV. Thus, a one percent change in output current from the current source of 0.01 mA will produce a 10 mV change in the voltage across the resistor. This is a ten percent error, and in typical actual circuits the error will be at least ten percent, and typically higher.

In addition, the total voltage across the circuit is typically 3.3 V or more, which means that the pacer must have a voltage doubler in it to produce this voltage. This of course results in increased complexity and power consumption or the driving circuitry. Since the voltage measured is analog, an analog-to-digital converter is also required, making the circuitry required in the pacer even more complex, and further increasing power consumption.

It may therefore be appreciated that there exists a substantial need for an improved oxygen sensor which is both highly accurate and not significantly sensitive to variations occurring in the supply current. Accordingly, it is the primary objective of the present invention to provide an improved oxygen sensor having both the required high degree of accuracy in sensing oxygen saturation and a low level of sensitivity to the occurrence of variations in the level of supply current used to drive the device. It is also a primary objective of the improved oxygen sensor of the present invention that it be capable of being driven by a drive circuit not requiring a voltage doubler, thereby reducing both the complexity and the power consumption of the driving circuitry.

It is a further objective of the present invention that it not require an analog-to-digital converter on the output of the circuit, thereby further reducing both the complexity and the power consumption of the device. The oxygen sensor as used in the implementation of a physiological response variable rate pacemaker must retain the desirable features of fast response, long term reliability, and high specificity. It is also an objective that all of the aforesaid advantages and objectives be achieved without incurring any substantial relative disadvantage.

SUMMARY OF THE INVENTION

The disadvantages and limitations of the background art discussed above are overcome by the present invention. With this invention, an oxygen sensor is disclosed which operates in a fundamentally different manner from previously known oxygen sensors. The oxygen sensor of the present invention uses an LED directly connected across a current source to fire the LED. The light from the LED is directed onto blood outside of the oxygen sensor, which reflects back a portion of the light onto a phototransistor. The phototransistor is not connected in series with the LED, as is the established manner of operating an oxygen sensor.

Rather, the phototransistor is connected to drive an integrator, which integrates the signal from the phototransistor from the time the LED is turned on. The integrator produces an output which is representative of the integrating operation performed on the signal from the phototransistor. The output of the integrator is provided to a threshold detector and latch, the latch of which threshold detector and latch is also connected across the LED. When the output of the integrator reached the threshold set in the threshold detector and latch, the latch of the threshold detector and latch will latch across the LED, causing the voltage across the LED to drop.

The amount of time that it takes from the time the LED is turned on for the voltage across the LED and the latch portion of the threshold detector and latch to drop is determined. The oxygen content of the blood is inversely related to the measured period of time, so once the time is known, the blood oxygen content may be determined. Thus, it is simple to determine the blood oxygen content by merely monitoring the voltage across the LED and the latch mechanism.

Thus, it is apparent that the maximum voltage which must be developed by the current source is the voltage across the LED prior to the latching operation occurring. The typical voltage across such an LED is approximately 1.6 V, which is less than the battery voltage of most pacers. Thus, the system of the present invention does not require the use of a voltage multiplier. This of course results in both a reduction in circuit complexity and a minimization of the amount of power required by the driving circuit.

In addition, the measured element is time rather than voltage, and only a simple digital circuit is required to measure the time period from the firing of the LED to the occurrence of the latching operation. Thus, the system of the present invention does not require the use of an analog-to-digital converter. This both eliminates a complex circuit and reduces the amount of power required to monitor the operation of the sensor.

It may therefore be seen that the present invention teaches an improved oxygen sensor having both the required high degree of accuracy in sensing oxygen content and a low level of sensitivity to the occurrence of variations in the level of supply current used to drive the device. The improved oxygen sensor of the present invention is capable of being driven by a drive circuit not requiring a voltage doubler, thereby minimizing the complexity and the power consumption of the driving circuitry.

The improved oxygen sensor of the present invention further does not require an analog-to-digital converter on the output of the circuit, thereby further minimizing the complexity and the power consumption of the device. The oxygen sensor of the present invention as used in the implementation of a truly physiological response variable rate pacemaker retains the desirable features of fast response, long term reliability, and very high specificity. Finally, all of the aforesaid advantages and objectives are achieved without incurring any substantial relative disadvantage.

DESCRIPTION OF THE DRAWINGS

These and other advantages of the present invention are best understood with reference to the drawings, in which.

DETAILED DESCRIPTION OF THE PREFERRED EMBODIMENT

The preferred embodiment of a pacemaker system employing the oxygen sensor of the present invention is illustrated in Figure The system has two components, the first of which is an electronic pulse generator 20, which is shown implanted in the right upper chest cavity. The second component is a pacing lead 22, one end of which is connected to the electronic pulse generator 20. The other end of the pacing lead 22 is implanted in a vein leading to the heart 24, with the distal end of the pacing lead 22 being located in the right ventricle of the heart 24.

Figure 1:
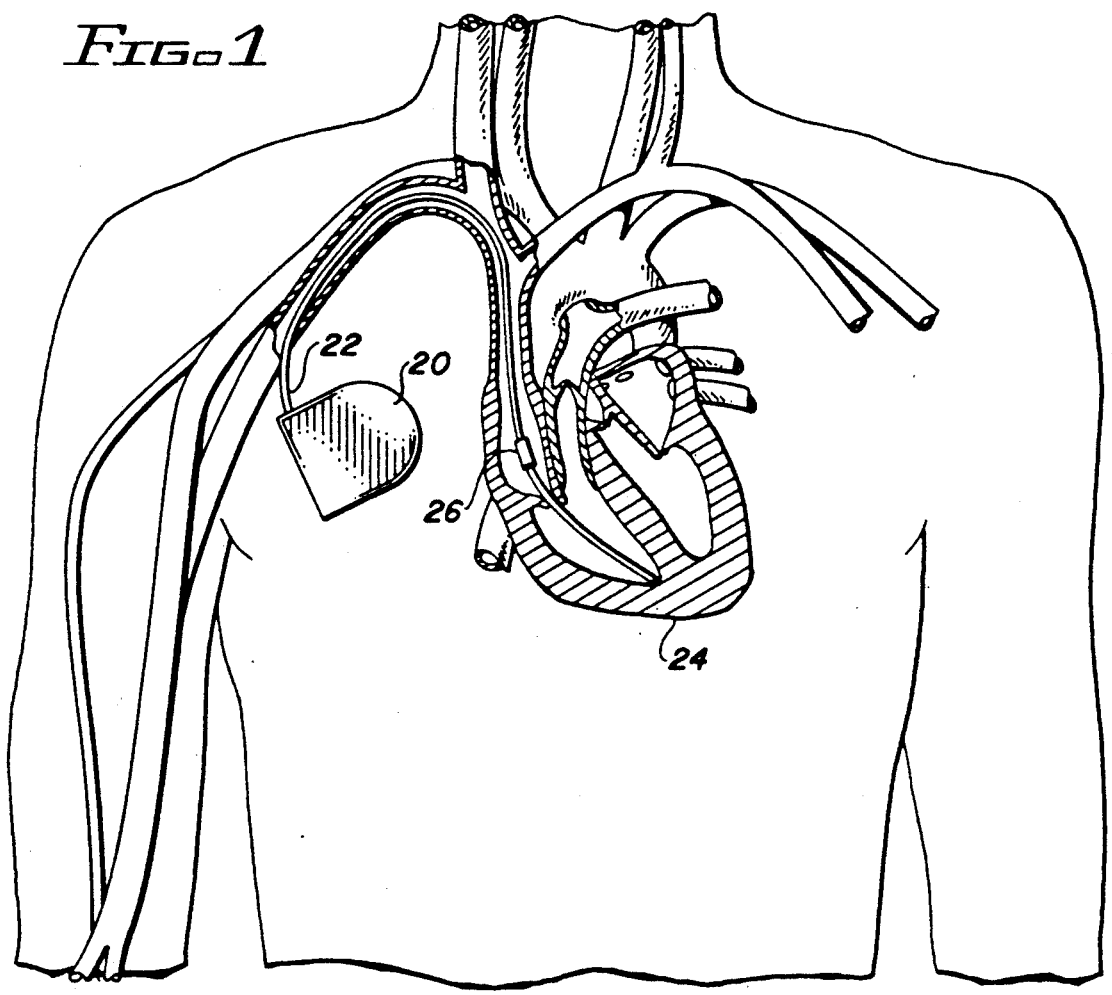
FIG. 1 is a diagrammatic illustration of the installation of the system of the present invention in the abdominal region of a human being.

The pacing lead 22 illustrated in FIG. 1 and in the other figures of this specification is a unipolar lead, although bipolar leads are well known in the art and could also be used. In addition, the electronic pulse generator 20 illustrated is a single chamber pacemaker, although the principles of the present invention are equally applicable to dual chamber pacemakers.

Disposed on the pacing lead 22 is an oxygen sensor 26, which is shown in the right atrium of the heart 24. The oxygen sensor 26 could also be disposed in the right ventricle of the heart 24. For an excellent discussion of the basic use of an oxygen sensing pacing system, see U.S. Pat. No. 4,815,469, to Cohen et al., which patent is assigned to the assignee of the present invention. U.S. Pat. No. 4,815,469 is hereby incorporated herein by reference.

Figure 2:
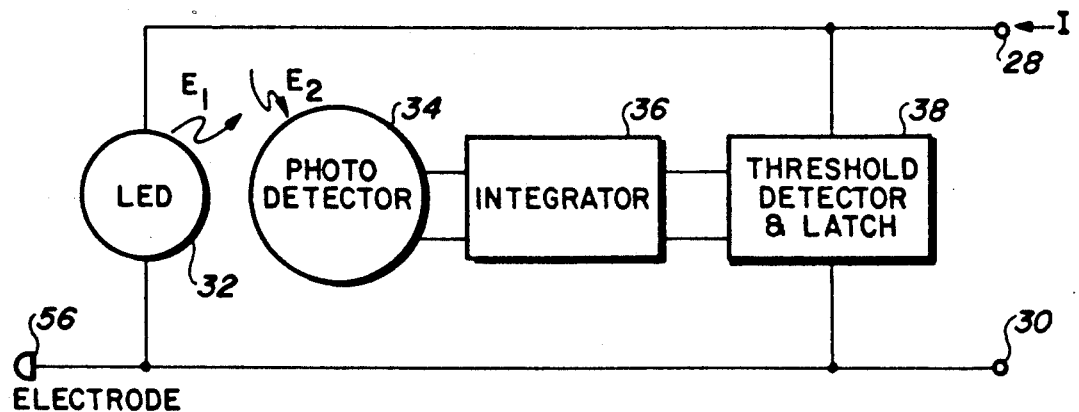
FIG. 2 is a is a schematic block diagram of the oxygen sensor of the present invention.

The oxygen sensor 26 of the present invention uses the functional design shown in FIG. 2. Like previously known systems, it is designed to be driven by a current source (not shown) across the terminals 28 and 30. An LED 32 is connected directly across the terminals 28 and 30, thus placing the LED 32 directly across the current source. As such, the current source will fire the LED 32, causing it to emit light energy $E_1$. In the preferred embodiment, the light energy $E_1$ has a wavelength of approximately 660 nM, a wavelength which has reflection properties indicative of the total oxygen content of the blood.

The light $E_1$ will come into contact with the blood, and, depending on the properties of the blood, a portion of the light energy $E_1$ will be reflected back to the oxygen sensor 26. A photodetector 34 is used to measure the amount of light reflected back to the oxygen sensor 26, with the amount of light energy reflected back to the photodetector 34 being identified as $E_2$. The amount of current that flows through the photodetector 34 will be proportional to the light energy $E_2$.

The current from the photodetector 34 is supplied to an integrator 36, which integrates the current from the photodetector 34 over time. The integrator 36 supplies as an output the integrated value of current from the photodetector 34. This output is supplied by the integrator 36 to a threshold detector and latch 38. The threshold detector and latch 38 compares the integrated value of current from the photodetector 34 to a preset threshold. When that threshold is reached, the threshold detector and latch 38 will latch across the terminals 28 and 30.

Prior to the time that the threshold detector and latch 38 latches across the terminals 28 and 30, the voltage across the terminals 28 and 30 is a function of the LED 32. This voltage is referred to as VI, and in a typical case will be approximately 1.6 V. At this time, the latch portion of the threshold detector and latch 38 is off and does not consume current. When the output from the integrator 36 reaches the threshold of the threshold detector and latch 38, the latch portion of the threshold detector and latch 38 will latch, causing the voltage across the terminals 28 and 30 to drop to a voltage $V_2$.

By measuring the amount of time that it takes from the point that the LED 32 is energized to emit light to the time that the threshold detector and latch 38 latches, a determination can be made of the oxygen content of the blood. The greater the oxygen content of the blood, the more light will be reflected to the photodetector 34. Thus, the shorter the time that the threshold detector and latch 38 takes to latch, the higher is the total oxygen content of the blood.

Figure 3:
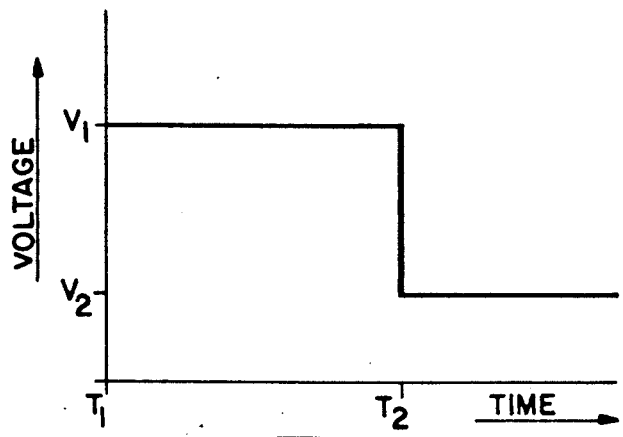
FIG. 3 is a timing diagram showing the voltage across the oxygen sensor of FIG. 2 plotted against time.

Referring now to FIG. 3 in conjunction with FIG. 2, an illustration of this operation may be made. The integrator 36 is reset prior to the beginning of the operation. The latch portion of the threshold detector and latch 38 is also off at this time since the output of the integrator 36 (zero) is below the threshold. At time $T_1$, the current generator fires the LED 32, causing it to begin to emit the light energy $E_1$. At this time, the voltage across the terminals 28 and 30 is $V_1$.

The light energy $E_2$ is reflected to the photodetector 34, causing it to supply a current output to the integrator 36, which begins to integrate the current output of the photodetector 34. The threshold detector and latch 38 continuously checks the integrated current output of the photodetector 34 to determine whether it has reached the threshold. The integrated current output of the photodetector 34 reaches the threshold of the threshold detector and latch 38 at time $T_2$, at which point the latch portion of the threshold detector and latch 38 will latch.

When the latch portion of the threshold detector and latch 38 latches, the voltage across the terminals 28 and 30 will drop from $V_1$ to $V_2$. By monitoring the voltage across the terminals 28 and 30, the times $T_1$ and $T_2$ can be determined. The difference in time between $T_2$ and $T_1$ is indicative of the total oxygen content of the blood. Accordingly, those skilled in the art will realize that this time difference is a parameter which is a true physiological indicator which may be used to control a demand pacemaker.

Figure 4:
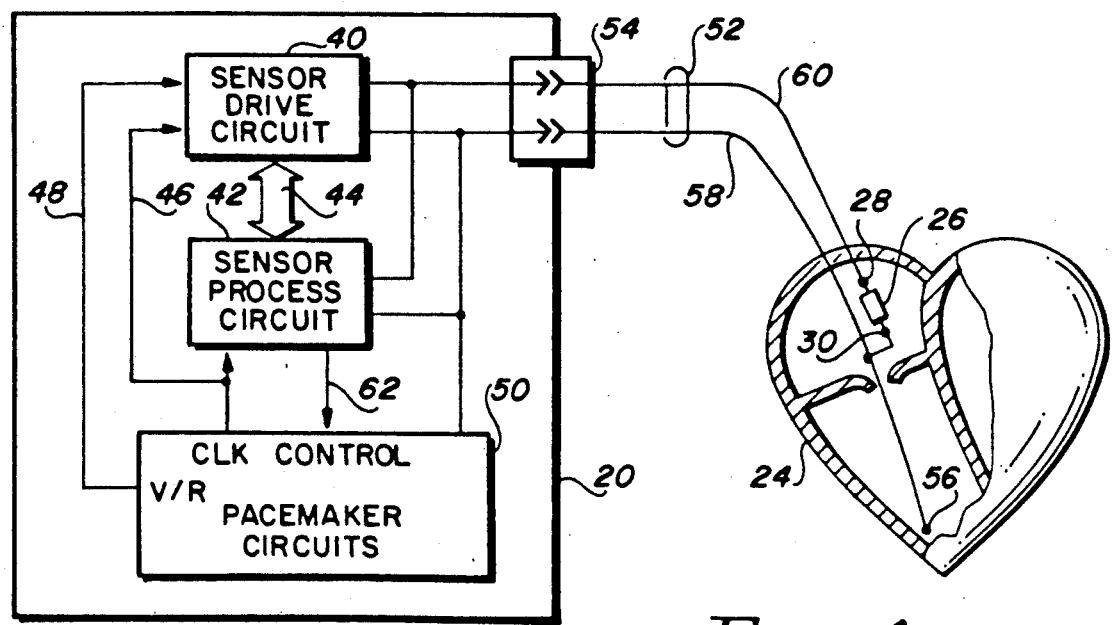
FIG. 4 is a schematic block diagram showing the basic operation of the pacemaker system for operating the oxygen sensor shown in FIG. 1.

Referring next to FIG. 4, a block diagram is shown illustrating the manner in which the oxygen sensor 26 is used to sense the reflective properties of blood in conjunction with control circuitry in the electronic pulse generator 20. The oxygen sensor 26 is positioned within an area of a living body where blood 44 is able to come in contact with the light energy $E_1$ emitted by the sensor. Typically, the oxygen sensor 26 will be placed within a vein that is carrying blood back to the heart, or within the heart 24 itself. FIG. 4 shows the oxygen sensor 26 placed in the right atrium of the heart 24.

A sensor drive circuit 40 provides the current pulse needed to drive the oxygen sensor 26. Similarly, a sensor process circuit 42 monitors the voltage developed across the sensor terminals 28 and 30. Appropriate timing signals 44 are shared between the sensor drive circuit 40 and the sensor process circuit 42. Further, in order to synchronize the sensing function of the oxygen sensor 26 with other events, the sensor drive circuit 40 and the sensor process circuit 42 typically receive a clock signal 46 and a timing reference signal 48 from a location external to these circuits.

For example, when the sensor 42 is used with an implanted electronic pulse generator 20, the clock signal 46 is obtained from the circuits within the electronic pulse generator 20. Similarly, the reference signal 48 is typically a signal indicating a cardiac event, such as a V-pulse or an R-wave signal, which signals indicate that the ventricle of the heart has either been paced or that a ventricular contraction has been sensed.

The drive circuit 40 and the sensor circuit 42 are included within the electronic pulse generator 20, which electronic pulse generator 20 is made to be implantable in a human body. Also included within the electronic pulse generator 20 are conventional pacemaker circuits 50, which are well known in the art. The drive circuit 40 and the sensor circuit 42 are coupled to the pacemaker circuits 50 in the manner above-described. That is, the clock signal 46, as well as a V/R signal 48 (signifying either an R-wave has been sensed or a V-stimulation pulse has been generated) are provided from the pacemaker circuits 50 to the drive circuit 40 and the sensor circuit 42.

A pacing lead 52, connected to the electronic pulse generator 20 by way of a conventional bipolar pacer connector 54, allows the electronic pulse generator 20 to deliver stimulation pulses to the heart 24 at a distal electrode 56 through conductor 58. This same conductor 58 allows the pacemaker circuits 50 to sense cardiac events occurring near the electrode 56. The oxygen sensor 26 is advantageously embedded within the pacemaker lead 52 at a location spaced apart from the electrode 56 so as to place the oxygen sensor 26 within the right atrium of the heart 24.

Further, when positioned properly within the heart, the pacemaker lead 52 is curved in a manner that causes the oxygen sensor 26 to face blood just prior to the blood's passage through the tricuspid valve of the heart 24. The terminal 28 of the oxygen sensor 26 is connected to a separate conductor 60 of the lead 52. The other terminal 30 of the oxygen sensor 26 is connected within the pacemaker lead 52 to the conductor 60.

The sensor process circuit 42 monitors the time difference between $T_2$ and $T_1$, develops a control signal 62 which is a function of this time difference. The control signal 62 is thus representative of the reflectance properties of the blood (and hence relatable to the amount of oxygen which has been sensed within the blood). This control signal 62 is presented to the pacemaker circuits 50, and is used as a physiological parameter to control the rate at which the electronic pulse generator 20 delivers a stimulation pulse to the heart 24. Thus, the system shown in FIG. 4 is representative of a rate-responsive pacemaker wherein the rate of the pacemaker varies as a function of the sensed oxygen content of the blood that comes in contact with the oxygen sensor 26.

Figure 5:
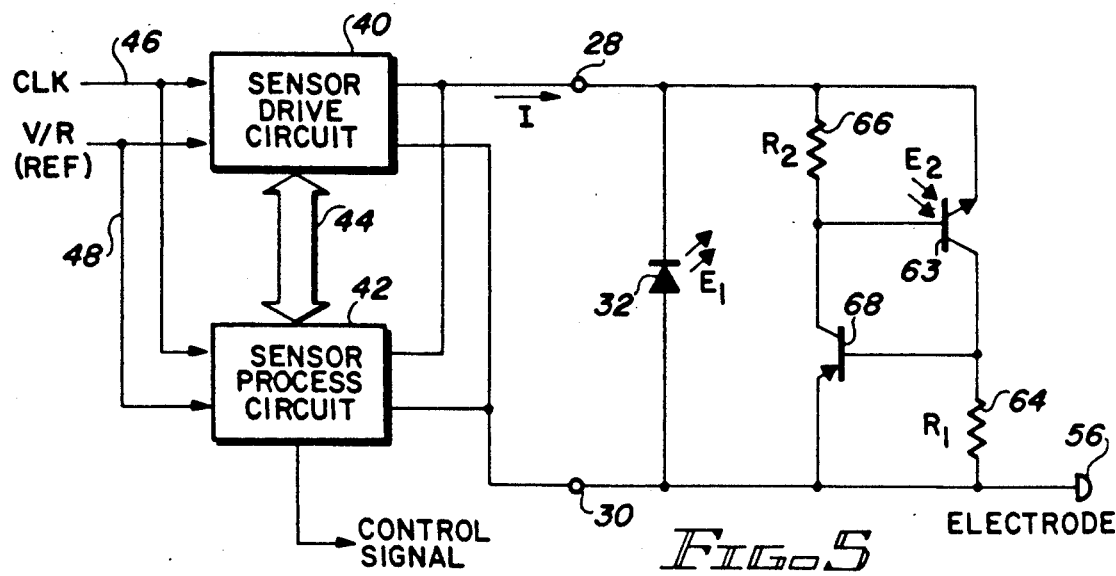
FIG. 5 is a schematic block diagram showing one possible electrical design for the oxygen sensor of the present invention is conjunction with the portion of the pacemaker system operating the oxygen sensor.

Referring next to FIG. 5, one possible circuit schematic for the oxygen sensor 26 is shown in conjunction with portions of the control system for the oxygen sensor 26, including the sensor drive circuit 40, the sensor process circuit 42, and the various control signals associated therewith. The LED 32 in the preferred embodiment is a GaAlAs LED emitting light at a wavelength of approximately 660 nM. The cathode of the LED 32 is connected to the terminal 28, and the anode of the LED 32 is connected to the terminal 30.

The photodetector 34 used is an NPN phototransistor 63, having its emitter connected to the terminal 28. A first resistor 64 having a value RI is connected between the collector of the phototransistor 63 and the terminal 30. A second resistor 66 having a value R2 is connected across the base-emitter junction of the phototransistor 63. Finally, a PNP transistor 68 has its collector connected to the base of the phototransistor 63, its base connected to the collector of the phototransistor 63, and its emitter connected to the terminal 30.

The second resistor 66 is very small compared to the first resistor 64, differing by approximately two orders of magnitude. For example, the first resistor 64 may be a 20 MΩ resistor, and the second resistor 66 may be a 220 KΩ resistor. The betas of the phototransistor 63 and the transistor 68 are both high, being approximately 200.

There are five capacitances which need to be considered in an analysis of the operation of the circuit. The first capacitance is that of the feedthrough capacitors in the pacer connector 54, which capacitors are not illustrated. The other four capacitances are characteristics of the phototransistor 63 and the transistor 68.

The phototransistor 63 has a capacitance between its base and emitter (across the second resistor 66), which capacitance shall be called $C_{BEnpn}$. The phototransistor 63 also has a capacitance across its collector and base, which capacitance shall be called $C_{CBnpn}$. The transistor 68 has a capacitance across its collector and base, which capacitance shall be called $C_{CBpnp}$. Finally, the transistor 68 has a capacitance across its base and emitter, which capacitance shall be called $C_{BEpnp}$. Capacitances $C_{CBnpn}$ and $C_{CBpnp}$ are in parallel, and may be referred to together as $C_\mu$.

Figure 6:
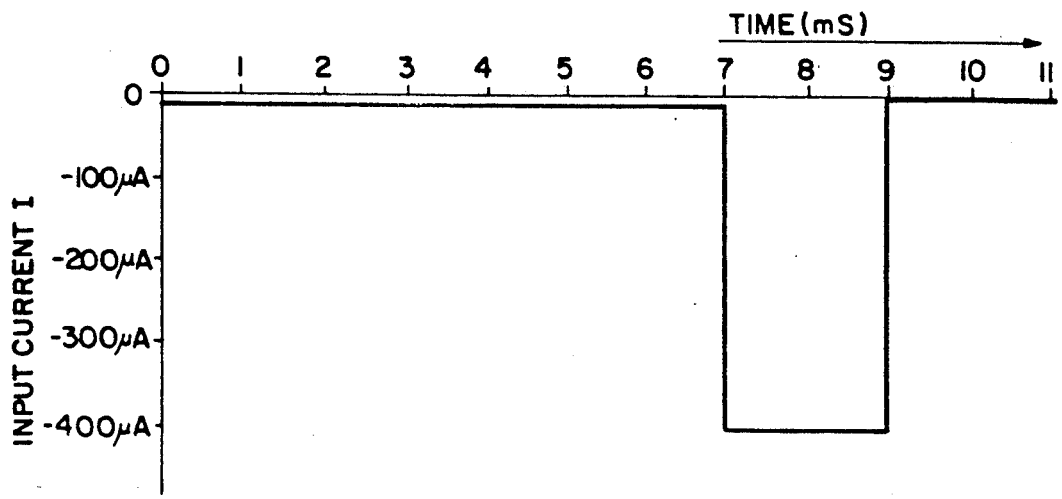
FIG. 6 is a timing diagram showing the current supplied from the current generator of the drive circuit to operate the oxygen sensor of FIG. 5.
Figure 7:
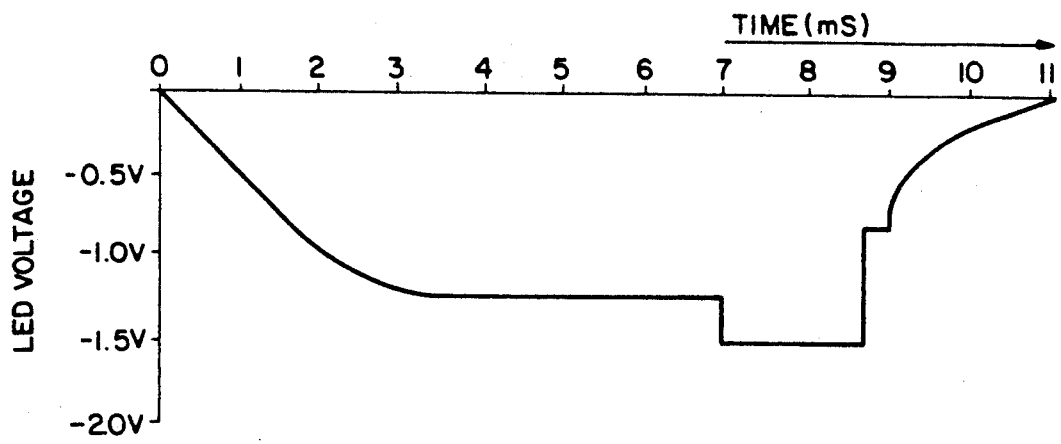
FIG. 7 is a timing diagram showing the voltage across the oxygen sensor of FIG. 5.
Figure 8:
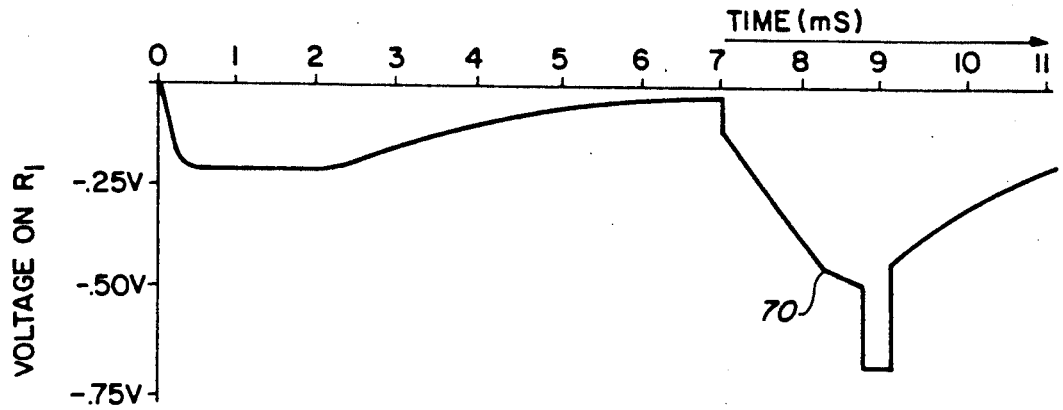
FIG. 8 is a timing diagram showing the voltage across the resistor $R_1$ of the oxygen sensor of FIG. 5.

Referring now to FIGS. 6–8 in addition to FIG. 5, the input current to the circuit, the voltage across the circuit, and the voltage across the first resistor 64 (and across $C_{BEpnp}$) are shown. A small initialization current prior to firing the LED 32 is necessary for three separate reasons. First, it is necessary to control the voltage across the first resistor 64 in order to prevent the circuit from immediately latching without any light being generated by the LED 32. Thus, the rate of change of voltage across the LED 32 (and thus across the sensor) with respect to time must be carefully limited. This is due to the presence of the feedthrough capacitors.

Secondly, the initialization current is necessary to reach the onset of current conduction in the LED 32. Thirdly, the initialization current is necessary until the voltage across the first resistor 64 returns nearly to zero. The reason for this last requirement is again to prevent premature latching and inaccuracy of measurement.

Referring specifically to FIG. 6, it may be seen that only a very small initialization current is necessary, on the order of −1 μA. (All currents and voltages are negative in FIGS. 6–8 due to the current direction of FIG. 5.) It may be seen that there is a ramp from 0 to approximately −1.30 V in the voltage across the LED 32. This ramp is due to the feedthrough capacitors. The voltage across the first resistor 64 is initially approximately the differential of the voltage across the LED 32, so it will be appreciated that it is critical to keep the slope of voltage across the LED 32 limited to avoid premature latching.

The voltage across the LED 32 levels out at approximately −1.3 V as the LED 32 begins to conduct. However, only a negligible amount of light is emitted during this stage as the LED 32 begins to conduct. Meanwhile, the voltage across the first resistor 64 returns to a nominal amount, approximately 100–300 mV. This return of the voltage across the first resistor 64 is again necessary to avoid preliminary latching.

The point of integration is an integration node, which is the collector of the phototransistor 63, the base of the transistor 68, and the one side of the first resistor 64. The integrating capacitance is thus $C_\mu$ plus $C_{BEpnp}$. (Note also that the integrating node could be at the base of the phototransistor 63, in which case the value of the first resistor 64 would be small, the value of the second resistor 66 would be high, and the integrating capacitance would be $C_\mu$ plus $C_{BEnpn}$.) Prior to firing the LED 32, the voltage at this integration node is the voltage across the first resistor 64, which is a small value. During the entire initialization process, both the LED 32 and the transistor 68 are off.

The LED 32 is fired by a −100 to −400 μA spike in current, as seen in FIG. 6. At this time, the voltage across the LED 32 increases in magnitude to approximately −1.55 V, and the LED 32 begins to emit light which may be reflected by the blood onto the phototransistor 63. Simultaneously, the voltage across the first resistor 64 (and on the integrating node) increases in magnitude to approximately −100 mV.

Photocurrent begins to flow through the base collector junction of the phototransistor 63, which acts like a photodiode. This current flows through the second resistor 66 (which due to its relatively small value acts as a short circuit), and begins to charge the capacitance $C_{BEpnp}$, which is across the first resistor 64. Both the phototransistor 63 and the transistor 68 are still off at this point.

As the voltage across the first resistor 64 increases, the transistor 68 comes closer and closer to beginning to turn on. Since the second resistor 66 is much smaller than the first resistor 64 (and thus the voltage across the second resistor 66 is smaller than the voltage across the first resistor 64), the phototransistor 63 is still off. There is a knee in the voltage across the first resistor 64 shown in FIG. 8 designated by the reference numeral 70. This knee 70 is the point at which the voltage across the first resistor 64 begins to turn the transistor 68 on.

As the transistor 68 begins to turn on, current will flow through the base emitter junction, causing a current amplified by the high beta of the transistor 68 to flow from the emitter to the collector, and then through the second resistor 66. This increases the voltage across the second resistor 66. In short order both the phototransistor 63 and the transistor 68 will conduct, latching the circuit.

As the circuit latches, the voltage across the phototransistor 63 drops sharply, as shown in FIG. 7. By measuring the time between the beginning of the −400 μA current step and the sharp drop in voltage across the LED 32, an indication of the oxygen content of the blood may be determined. The oxygen content of the blood is inversely related to this time, and the system has been found to be highly accurate across a wide range of blood oxygen content.

It is to be noted that the maximum voltage across the circuit of the present invention is approximately 1.55 V, which is significant in that a voltage multiplier is not necessary in the construction of the driving circuits. In addition, since the time is measured rather than voltage, no analog-to-digital converter is necessary. Thus, the system of the present invention requires less circuit complexity and less power.

It may therefore be appreciated from the above detailed description of the preferred embodiment of the present invention that it teaches an improved oxygen sensor having both the required high degree of accuracy in sensing oxygen content and a low level of sensitivity to the occurrence of variations in the level of supply current used to drive the device. The improved oxygen sensor of the present invention is capable of being driven by a drive circuit not requiring a voltage doubler, thereby minimizing the complexity and the power consumption of the driving circuitry.

The improved oxygen sensor of the present invention further does not require an analog-to-digital converter on the output of the circuit, thereby further minimizing the complexity and the power consumption of the device. The oxygen sensor of the present invention as used in the implementation of a truly physiological response variable rate pacemaker retains the desirable features of fast response, long term reliability, and very high specificity. Finally, all of the aforesaid advantages and objectives are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A blood oxygen sensor for use with a pacemaker to sense the level of oxygen in blood, said blood oxygen sensor comprising:

an LED for emitting light;
   means for driving said LED to emit light beginning at a first time;
   means for directing the light emitted by said LED onto blood and for allowing light reflected by blood to return to the sensor;
   a photodetector for detecting the portion of light from said LED which is reflected by blood and returned to the sensor, said photodetector providing an output proportional to the portion of light from said LED which is reflected by blood;
   an integrator for integrating said output from said photodetector and providing as an output an integrated voltage output;
   means for determining a predetermined threshold value;
   means for comparing said integrated voltage output with said predetermined threshold value and providing an output signal at a second time when said integrated voltage output reaches said predetermined threshold value; and a
   means for monitoring the interval between said fist time and said second time and providing an output signal indicative of the interval between said first time and aid second time, the interval between said first time and said second time being inversely related to the level of oxygen in blood.

2. A blood oxygen sensor as defined in claim 1, wherein said LED comprises:
   an LED which emits light at a wavelength of approximately 660 nM.

3. A blood oxygen sensor as defined in claim 1, additionally comprising:
   a first conductor for connection to a pacemaker at one end thereof;
   a second conductor for connection to a pacemaker at one end thereof, said LED being connected across said first and second conductors and said means for driving being electrically connected across said first and second conductors.

4. A blood oxygen sensor as defined in claim 3, wherein said means for driving comprises:
   means for supplying a current pulse, said first and second conductors having a first voltage therebetween when said LED is driven by said current pulse, said output signal provided by said comparing means being characterized by a second voltage between said first and second conductors.

5. A blood oxygen sensor as defined in claim 4, wherein said second voltage is less than said first voltage.

6. A blood oxygen sensor as defined in claim 4, wherein said comparing mean comprises:
   means for latching connected between said first and second conductors, said output signal being provided by said latching means latching between said first and second conductors to cause the voltage therebetween to change from said first voltage to said second voltage.

7. A blood oxygen sensor as defined in claim 1, wherein said photodetector comprises:
   a phototransistor.

8. A blood oxygen sensor as defined in claim 7, wherein said integrator and comparing means comprise:
   a transistor, the collector of said transistor being connected to the base of said phototransistor, the base of said transistor being connected to the collector of said phototransistor, the emitter of said transistor being connected to said second conductor, the emitter of said phototransistor being connected to said first conductor;
   a first transistor connected across the base emitter junction of said transistor; and
   a second resistor connected across the base emitter junction of said phototransistor.

9. A blood oxygen sensor as defined in claim 8, wherein said transistor is a PNP transistor, and said phototransistor is an NPN phototransitor.

10. A blood oxygen sensor as defined in claim 8, wherein said first resistor has a substantially larger resistance than said secondresitor.

11. A blood oxygen sensor as defined in claim 8, wherein the cathode of said LED is connected to said first conductor, and the anode of said LED is connected to said second conductor.

12. A blood oxygen sensor as defined in claim 8, wherein said means for driving supplies an initialization current to said LED prior to said first time.

13. A blood oxygen sensor as defined in claim 12, wherein said initialization current is sufficiently small to limit the voltage across said first resistor to a value not sufficient to cause latching.

14. A blood oxygen sensor as defined in claim 12, wherein said means for driving supplies a current pulse to said LED beginning at said first time.

15. A blood oxygen sensor for use with a pacemaker to sense the level of oxygen in blood, said blood oxygen sensor comprising:
   a first conductor for connection to a pacemaker at one end thereof;
   a second conductor for connection o a pacemaker at one end thereof;
   an LED connected between said first and second conductors, said LED for emitting light;
   means for driving said LED to emit light beginning at a first time, said means for driving being electrically connected between said first and second conductors;
   means for directing the light emitted by said LED onto blood and for allowing light reflected by blood to return to the sensor;
   a phototransmistor for detecting the portion of light from said LED which is reflected by flood and returned to the sensor, the emitter of said phototransistor being connected to said first conductor;
   a transistor, the collector of said transistor being connected to the base of said phototransistor, the base of said transistor being connected to the collector of said phototransistor, the emitter of said transistor being connected to said second conductor;
   a first resistor connected across the base-emitter junction of said transistor;
   a second resistor connected across the base-emitter junction of said phototransistor, said transistor and said phototransistor conducting at a second time dependant on the amount of light reflected by blood to said phototransistor; and
   means for monitoring the interval between said first time and aid second time and providing an output signal indicative of the interval between said first time and said second time, the interval between said first time and said second time being inversely related to the level of oxygen in blood.

16. A blood oxygen sensor as defined in claim 15, wherein said means for driving comprises:
   means for supplying a current pulse, said first and second conductors having a first voltage therebetween when said LED is driven by said current pulse, said output signal provided by said comparing means being characterized by a second voltage between said first and second conductors.

17. A blood oxygen sensor as defined in claim 15, wherein said comparing means comprises:
   means for latching connected between said first and second conductors, said output signal being provided by said latching means latching between said first and second conductors to cause the voltage therebetween to drop from said first voltage to said second voltage.

18. A blood oxygen sensor as defined in claim 15, wherein said transistor is a PNP transistor, and said phototransistor is an NPN phototransistor.

19. A blood oxygen sensor as defined in claim 15, wherein said first resistor has a substantially larger resistance than said second resistor.

20. A blood oxygen sensor as defined in claim 15, wherein the cathode of said LED is connected to said first conductor, and the anode of said LED is connected to said second conductor.

21. A blood oxygen sensor as defined in claim 15, wherein said means for driving supplies an initialization current to said LED prior to said first time.

22. A blood oxygen sensor as defined in claim 21, wherein said initialization current is sufficiently small to limit the voltage across said first resistor to a value not sufficient to cause lacking.

23. A blood oxygen sensor as defined in claim 21, wherein said means for driving supplies a current pulse to said LED beginning at said first time.

24. A blood oxygen sensor for use with a pacemaker, said blood oxygen sensor comprising:
   means for emitting light beginning at a first time;
   means for directing the light emitted by said emitting means onto blood and for flowing light reflected by blood to return to the sensor;
   means for detecting the portion of light from said emitting means which is reflected by blood and returned to the sensor, said detecting means providing an output proportional to the portion of light from said emitting means which is reflected by blood;

means for integrating said output from said detecting means and providing as an output an integrated voltage output;

means for determining a predetermined threshold value;

means for comparing said integrated voltage output with said predetermined threshold value and providing an output signal at a second time when said integrated voltage output reaches said predetermined threshold value; and means for monitoring the interval between said first time and said second time and providing an output signal indicative of the interval between said first time and said second time, the interval between said first time and said second time being inversely related to the level of oxygen in said blood.

25. A method of determining the level of blood oxygen suing a sensor, said method comprising:

driving an LED to emit light beginning at a first time;

directing the light emitted by said LED onto blood and allowing light reflected by blood to return to the sensor;;

detecting the portion of light from said LED which is reflected by said blood and returned to the sensor with a photodetector, said photodetector providing an output proportional to the portion of light from said LED which is reflected by said blood;

integrating said output from said photodetector with an integrator and providing as an output of said integrator an integrated voltage output;

comparing said integrated voltage output with a predetermined threshold value and providing an output signal at a second time when said integrated voltage output reaches said predetermined threshold value; and monitoring the interval between said first time and said second time and providing an output signal indicative of the interval between said first time and said second time, the interval between said first time and said second time being inversely related to the level of oxygen in said blood.

* * * * *